(12) United States Patent
Sugino et al.

(10) Patent No.: US 7,147,328 B2
(45) Date of Patent: Dec. 12, 2006

(54) OPHTHALMOLOGIC PHOTOGRAPHING APPARATUS

(75) Inventors: Yuichi Sugino, Tokyo (JP); Tomoyoshi Abe, Tokyo (JP); Takanori Takeda, Tokyo (JP); Taisaku Kogawa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 452 days.

(21) Appl. No.: 10/413,571

(22) Filed: Apr. 15, 2003

(65) Prior Publication Data
US 2004/0004694 A1    Jan. 8, 2004

(30) Foreign Application Priority Data
Apr. 19, 2002    (JP) ............................. 2002-118229

(51) Int. Cl.
*A61B 3/14*    (2006.01)
(52) U.S. Cl. .................. 351/206; 351/200; 351/205; 351/221
(58) Field of Classification Search ................ 351/205, 351/206, 221
See application file for complete search history.

(56) References Cited

U.S. PATENT DOCUMENTS

| | | | | |
|---|---|---|---|---|
| 5,181,055 A | * | 1/1993 | Sano et al. | 351/206 |
| 5,291,231 A | * | 3/1994 | Hideshima et al. | 351/208 |
| 5,355,895 A | * | 10/1994 | Hay | 351/211 |
| 5,374,967 A | * | 12/1994 | Hideshima et al. | 351/208 |
| 5,424,788 A | * | 6/1995 | Satake et al. | 351/206 |
| 5,579,063 A | * | 11/1996 | Magnante et al. | 351/211 |
| 5,594,512 A | * | 1/1997 | Yoneda et al. | 351/206 |
| 5,609,159 A | * | 3/1997 | Kandel et al. | 351/221 |
| 6,654,553 B1 | * | 11/2003 | Shibata et al. | 396/18 |

FOREIGN PATENT DOCUMENTS

| | | |
|---|---|---|
| JP | 08-112257 | 5/1996 |
| JP | 2001-245851 | 9/2001 |

* cited by examiner

*Primary Examiner*—Charles A Marmer, II
*Assistant Examiner*—John R Sanders
(74) *Attorney, Agent, or Firm*—Armstrong, Kratz, Quintos, Hanson & Brooks, LLP (57) ABSTRACT

An ophthalmologic photographing apparatus including: an apparatus main body having an illumination system for illuminating an eye to be examined and an observation system for observing an image of the eye to be examined which is illuminated by the illumination system; a photographing device for taking a light flux from the eye to be examined from an optical path of the observation system, photographing the image of the eye to be examined and recording the image; a storage unit for storing a photographing condition related to the apparatus main body and a photographing processing condition related to the photographing device for each of plural kinds of photographing processing modes in photographing and storing the eye to be examined; a designating unit for designating a photographing processing mode for the eye to be examined; and a setting unit for reading out a photographing condition related to the apparatus main body and a photographing processing condition related to the photographing device for a corresponding photographing processing mode from the storage unit according to designation by the designating unit and setting the photographing condition related to the apparatus main body and the photographing processing condition related to the photographing device.

1 Claim, 10 Drawing Sheets

| PHOTOGRAPHING PROCESSING MODE | | | |
|---|---|---|---|
| 1 | | OBSERVATION MAGNIFICATION (PHOTOGRAPHING MAGNIFICATION): 16(1.6)<br>SLIT WIDTH: FULL SIZE<br>AMOUNT OF PHOTOGRAPHING LIGHT: 3-4<br>ILLUMINATION ANGLE: 10-30°<br>BACKGROUND ILLUMINATION: NOT CONDUCTED<br>DIFFUSION LENS: USED<br>POINT: UNIFORM ILLUMINATION USING DIFFUSION LENS | 101 |
| 2 | | OBSERVATION MAGNIFICATION (PHOTOGRAPHING MAGNIFICATION): 16(1.6)<br>SLIT WIDTH: EXTRA FINE<br>AMOUNT OF PHOTOGRAPHING LIGHT: 4-5<br>ILLUMINATION ANGLE: 30-90°<br>BACKGROUND ILLUMINATION: L OR H IF NECESSARY<br>DIFFUSION LENS: NOT USED<br>POINT: INCREASE AMOUNT OF PHOTOGRAPHING LIGHT IN CASE OF EXTRA THIN SLIT | 102 |
| 3 | | OBSERVATION MAGNIFICATION (PHOTOGRAPHING MAGNIFICATION): 25(2.5)<br>SLIT WIDTH: MIDDLE<br>AMOUNT OF PHOTOGRAPHING LIGHT: 3-4<br>ILLUMINATION ANGLE: 30-60°<br>BACKGROUND ILLUMINATION: NOT CONDUCTED<br>DIFFUSION LENS: NOT USED<br>POINT: ILLUMINATE VICINITY OF PHOTOGRAPHING REGION AND PHOTOGRAPH USING REFLECTION LIGHT | 103, 104 |
| 4 | | OBSERVATION MAGNIFICATION (PHOTOGRAPHING MAGNIFICATION): 25(2.5)<br>SLIT WIDTH: FULL SIZE<br>AMOUNT OF PHOTOGRAPHING LIGHT: 4-5<br>ILLUMINATION ANGLE: 10-30°<br>BACKGROUND ILLUMINATION: NOT CONDUCTED<br>DIFFUSION LENS: USED<br>POINT: COLOR WITH FLUORESCEIN AND USE BLUE FILTER | 105 |

FIG. 5

| PHOTOGRAPHING PROCESSING MODE | | | |
|---|---|---|---|
| 5 | | OBSERVATION MAGNIFICATION (PHOTOGRAPHING MAGNIFICATION): 16(1.6)<br>SLIT WIDTH: EXTRA FINE<br>AMOUNT OF PHOTOGRAPHING LIGHT: 4-5<br>ILLUMINATION ANGLE: 30-60°<br>BACKGROUND ILLUMINATION: L OR H IF NECESSARY<br>DIFFUSION LENS: NOT USED<br>POINT: INCREASE AMOUNT OF PHOTOGRAPHING LIGHT IN CASE OF EXTRA THIN SLIT | |
| 6 | | OBSERVATION MAGNIFICATION (PHOTOGRAPHING MAGNIFICATION): 25(2.5)<br>SLIT WIDTH: WIDE<br>AMOUNT OF PHOTOGRAPHING LIGHT: 3-4<br>ILLUMINATION ANGLE: 0°<br>BACKGROUND ILLUMINATION: L OR H IF NECESSARY<br>DIFFUSION LENS: NOT USED<br>POINT: IRRADIATE SLIT LIGHT COAXIAL WITH MICROSCOPE FROM EDGE OF MYDRIATIC PUPIL AND SHIFT MICROSCOPE SUCH THAT EYE FUNDUS REFLECTION BECOMES MAXIMUM | |
| 7 | | OBSERVATION MAGNIFICATION (PHOTOGRAPHING MAGNIFICATION): 25(2.5)<br>SLIT WIDTH: WIDE<br>AMOUNT OF PHOTOGRAPHING LIGHT: 2-3<br>ILLUMINATION ANGLE: 0-10°<br>BACKGROUND ILLUMINATION: NOT CONDUCTED<br>DIFFUSION LENS: NOT USED<br>POINT: ELIMINATE SURFACE REFLECTION OF GONIOSCOPE AND UTILIZE ROTATION TILT OF PHOTOGRAPHING SLIT | |

FIG. 6

| PHOTOGRAPHING PROCESSING MODE | 1<br>DIFFUSION ILLUMINATION | 2<br>DIRECT ILLUMINATION | 3<br>INDIRECT ILLUMINATION | 4<br>FLUORESCENCE MODE | 5<br>CRYSTALLINE LENS AND VITREOUS BODY | 6<br>DIAPHANOSCOPY | 7<br>EYE FUNDUS AND GONIOSCOPY |
|---|---|---|---|---|---|---|---|
| EXPOSURE TIME | Auto | 1/8S IN MAXIMUM | Auto | Auto | Auto | Auto | Auto |
| Fno. (DIAPHRAGM) | LARGE | Auto | Auto | Auto | LARGE | Auto | Auto |
| EXPOSURE CORRECTION | NOT CONDUCTED | + | NOT CONDUCTED | — | NOT CONDUCTED | NOT CONDUCTED | NOT CONDUCTED |
| SENSITIVITY | LOW | HIGH | HIGH | Auto | HIGH | Auto | Auto |
| GAMMA VALUE | NORMAL | NORMAL | — | + | + | NORMAL | NORMAL |
| PHOTOMETRIC AREA | AVERAGE | HIGH LIGHT REGION | SPOT IN CENTER | AVERAGE | CENTER AND NEGLECT HIGH LIGHT | CENTER AND NEGLECT HIGH LIGHT | CENTER AND NEGLECT DARK PORTION |
| SHARPNESS | NORMAL | NORMAL | NORMAL | + | NORMAL | + | + |
| CONTRAST | NORMAL | NORMAL | + | + | + | + | + |
| COLOR | NORMAL | NORMAL | NORMAL | EMPHASIZE GREEN | NORMAL | NORMAL | NORMAL |

| OPACITY OF CATARACT | BLUE GAIN OF COLOR IMAGE PICKUP DEVICE | AMOUNT OF PHOTOGRAPHING LIGHT |
|---|---|---|
| 1 (OPACITY DEGREE IS VERY LOW) | 9 (LARGE GAIN) | 9 (LARGE) |
| 2 | 8 | 8 |
| ... | ... | ... |
| 5 (OPACITY DEGREE IS SOMEWHAT HIGH) | 6 (MIDDLE GAIN) (REDUCE BLUE GAIN TO VALUE SMALLER THAN GENERAL SET VALUE) | 6 (MIDDLE) (REDUCE THE AMOUNT OF PHOTOGRAPHING LIGHT) |
| ... | ... | ... |
| 10 (STATE IN WHICH OPACITY DEGREE IS VERY HIGH) | 1 (SMALL GAIN) (ALMOST NO BLUE GAIN) | 1 (SMALL) (FURTHER REDUCE THE AMOUNT OF PHOTOGRAPHING LIGHT) |

OPHTHALMOLOGIC PHOTOGRAPHING APPARATUS

BACKGROUND OF THE INVENTION

1. Field of the Invention

The present invention relates to an ophthalmologic photographing apparatus.

2. Description of the Related Art

A slit lamp microscope used as a kind of ophthalmologic photographing apparatus is used in many cases for observing an eye to be examined by medical professions in an ophthalmologic field. In order to conduct photographing of an observation image of the eye to be examined by the slit lamp microscope, a photographing device such as a digital camera or a 35 mm still camera is disposed in the course of an observation optical path, various photographing modes such as a direct photographing mode and an indirect photographing mode are set, and observation light is led onto a photographing surface (image pickup surface).

When photographing of the eye to be examined is conducted using such a slit lamp microscope, setting of various conditions in a slit lamp microscope side, such as a photographing region, observation magnification (photographing magnification), a slit width, the amount of light for photographing, and an illumination angle, and setting of various conditions in a photographing device side, such as an exposure time, an aperture, presence or absence of exposure correction, a gamma value, and a contrast are required according to various photographing modes.

However, up to now, there are a number of combinations of photographing conditions according to photographing modes in the slit lamp microscope main body side and the photographing device side. Thus, it is difficult to suitably set these photographing conditions in a short time without keeping a person to be examined waiting, so that considerable experience is required.

Also, in an ophthalmologic photographing apparatus including a conventional eye fundus camera used in the case where a cataract resulting from an opacity of the crystalline lens of the eye to be examined is observed and photographed, a cataract mode is merely designated. Thus, the fact is that suitable setting to a condition related to the main body and a photographing condition related to the photographing device is not conducted according to the degree of opacity of a cataract.

SUMMARY OF THE INVENTION

The present invention has been made in view of the above circumferences. An object of the present invention is to provide an ophthalmologic photographing apparatus in which a photographing condition related to a main body and a photographing processing condition related to a photographing device for each of plural kinds of photographing processing modes in photographing an eye to be examined can be easily designated without requiring experience to conduct photography, an optimum photographing image can be simply obtained according to each of the photographing modes, and optimum photographing can be conducted according to the degree of opacity of a cataract.

In order to attain the above-mentioned object, according to a first aspect of the present invention, there is provided an ophthalmologic photographing apparatus including:

an apparatus main body having an illumination system for illuminating an eye to be examined and an observation system for observing an image of the eye to be examined which is illuminated by the illumination system;

a photographing device for taking a light flux from the eye to be examined from an optical path of the observation system, photographing the image of the eye to be examined and recording the image;

storage means for storing a photographing condition related to the apparatus main body and a photographing processing condition related to the photographing device for each of plural kinds of photographing processing modes in photographing and storing the eye to be examined;

designating means for designating a photographing processing mode to the eye to be examined; and setting means for reading out a photographing condition related to the apparatus main body and a photographing processing condition related to the photographing device for a corresponding photographing processing mode from the storage means according to designation by the designating means and setting the photographing condition related to the apparatus main body and the photographing processing condition related to the photographing device.

According to a second aspect of the present invention, with the arrangement of the first aspect of the invention, the ophthalmologic photographing apparatus is characterized in that for each of the photographing processing modes, the photographing condition related to the apparatus main body includes setting information related to observation magnification, a slit width, the amount of photographing light, an illumination angle, a matter whether background illumination is conducted or not, a matter whether the diffusion lens is used or not, and a kind of a light source of the illumination system, and the photographing processing condition related to the photographing device includes setting information related to an exposure time, a size of diaphragm, a matter whether exposure correction is conducted or not, sensitivity, a gamma value, a photometric area, sharpness, a contrast, a color, and gain control of a light receiving element in the photographing device.

According to the present invention, the photographing condition related to the main body and the photographing processing condition related to the photographing device for each of plural kinds of photographing processing modes in photographing the eye to be examined, which are stored in the storage means, are easily designated using the designating means by an examiner without requiring experience. Thus, the optimum image of the eye to be examined can be simply obtained according to the designated photographing processing mode.

Further, for each of the photographing processing modes, the photographing condition related to the apparatus main body includes setting information related to observation magnification, a slit width, the amount of photographing light, an illumination angle, a matter whether background illumination is conducted or not, a matter whether the diffusion lens is used or not, and a kind of a light source of the illumination system, and the photographing processing condition related to the photographing device includes setting information related to an exposure time, a size of diaphragm, a matter whether exposure correction is conducted or not, sensitivity, a gamma value, a photometric area, sharpness, a contrast, a color, and gain control of a light receiving element in the photographing device. Therefore, it becomes possible to optimally photograph each image of a lesion portion, a cornea cross section, a floater in a transparent body, a colored region in fluorescence photographing, a crystalline lens, an eye fundus, etc.

According to a third aspect of the present invention, there is provided an ophthalmologic photographing apparatus including:

an apparatus main body having a light source, an illumination system for irradiating an eye to be examined with illumination light and photographing light from the light source, and an observation system for observing an image of the eye to be examined which is illuminated by the illumination system;

a photographing device having a color image pickup device, for receiving a light flux from the eye to be examined from an optical path of the observation system by the color image pickup device, photographing the image of the eye to be examined and recording the image;

designating means for designating a cataract mode to the eye to be examined and a degree of opacity thereof; and control means for controlling a blue gain according to the degree of opacity based on designation of the designating means.

According to the present invention, blue gain adjustment is conducted according to a cataract mode to the eye to be examined and the degree of opacity. Thus, the eye to be examined which has suffered from a cataract can be optimally photographed according to the degree of opacity thereof.

According to a fourth aspect of the present invention, there is provided an ophthalmologic photographing apparatus including:

an apparatus main body having a light source, an illumination system for irradiating an eye to be examined with illumination light and photographing light from the light source, and an observation system for observing an image of the eye to be examined which is illuminated by the illumination system;

a photographing device having a color image pickup device, for receiving a light flux from the eye to be examined from an optical path of the observation system by the color image pickup device, photographing the image of the eye to be examined and recording the image;

detection means for detecting a degree of opacity of a cataract of the eye to be examined; and control means for controlling a blue gain according to the degree of opacity based on a detection result of the detection means.

According to the present invention, the degree of opacity of the eye to be examined is detected and blue gain adjustment to a color image pickup device is conducted according to the degree of opacity. Thus, the eye to be examined which has suffered from a cataract can be optimally photographed according to the degree of opacity thereof.

DETAILED DESCRIPTION OF THE PREFERRED EMBODIMENTS

Hereinafter, embodiments of the present invention will be described in detail.

(Embodiment 1)

Figure 1:
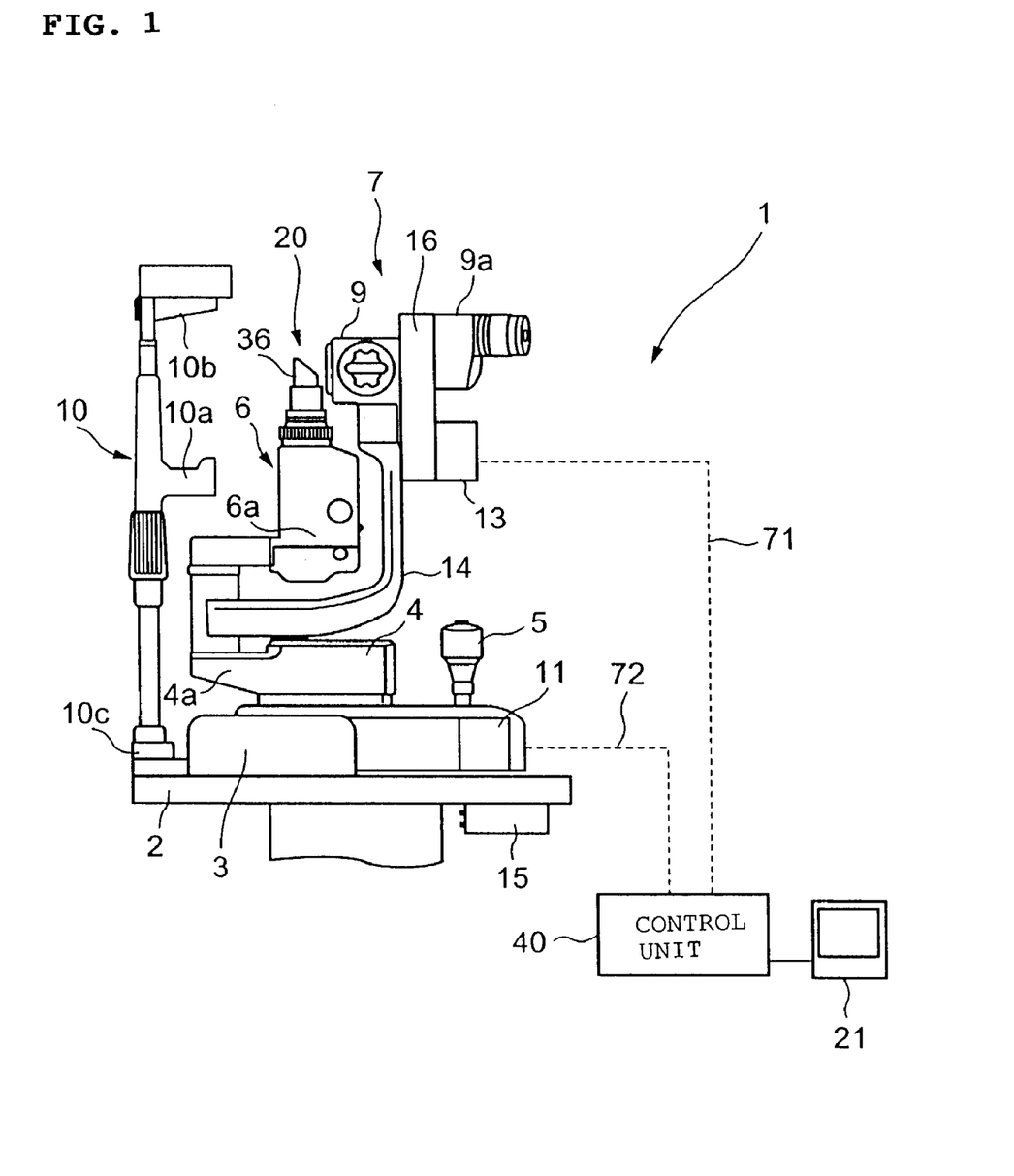
FIG. 1 is a schematic view showing the entire structure of an ophthalmologic photographing apparatus according to Embodiment 1 of the present invention.

An ophthalmologic photographing apparatus 1 of Embodiment 1 as shown in FIG. 1 includes an apparatus main body (hereinafter referred to as a main body) 20. The main body 20 is composed of a pedestal 11 which is supported by a movement mechanism portion 3 so as to be moveable horizontally in the lateral and longitudinal directions on an eye examination table 2, a base 4 supported in the vertical direction by the pedestal 11, an operating handle 5 for displacing the pedestal 11 horizontally in the lateral and longitudinal directions through tilting operation, an illumination system 6 having a light source portion 6a, a prism 12, and the like, which are supported by a protrusive axle shell 4a of the base 4 so as to be horizontally rotatable, an observation system 7 for observing an eye to be examined E, and a chin rest stand 10 having a chin rest 10a for person to be examined which is opposed to a barrel main body 9 housing an objective lens 31 of the observation system 7, a forehead holder 10b, and a base portion 10c set on the table 2.

The observation system 7 is rotatably supported by a support arm 14 which is substantially reverse-L shaped in side view and axially supported at one end by the protrusive axle shell 4a of the base 4. In addition, the illumination system 6 is supported rotatably to the upper side of one end of the support arm 14 by the protrusive axle shell 4a of the base 4.

A photographing device 13 composed of a digital camera is attached through a camera attachment 16 to a portion between the barrel main body 9 and an eyepiece barrel 9a in the observation system 7. A power source box 15 for supplying power to the light source portion 6a is located on the under surface of the table 2.

Figure 3:
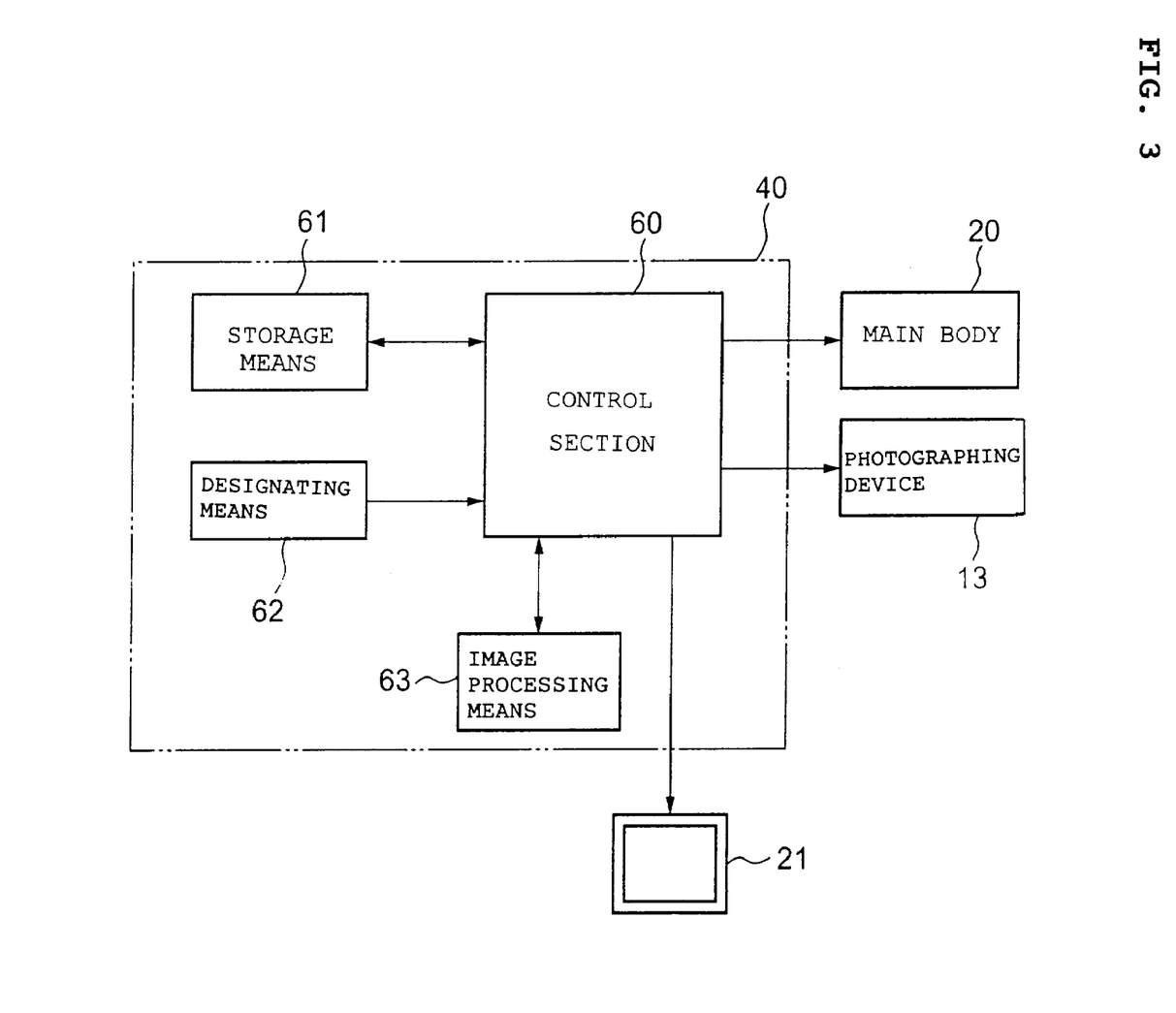
FIG. 3 is a block diagram of the control system in the ophthalmologic photographing apparatus according to Embodiment 1.

Further, as shown in FIGS. 1 and 3, in addition to the main body 20, the ophthalmologic photographing apparatus 1 has a control unit 40 including storage means 61, designating means 62, a control section 60, and image processing means 63 which are described later in detail, and an image monitor 21 for monitoring an image of the eye to be examined E.

Next, a structure of the optical system of the main body 20 of the ophthalmologic photographing apparatus 1 will be described with reference to FIG. 2.

Figure 2:
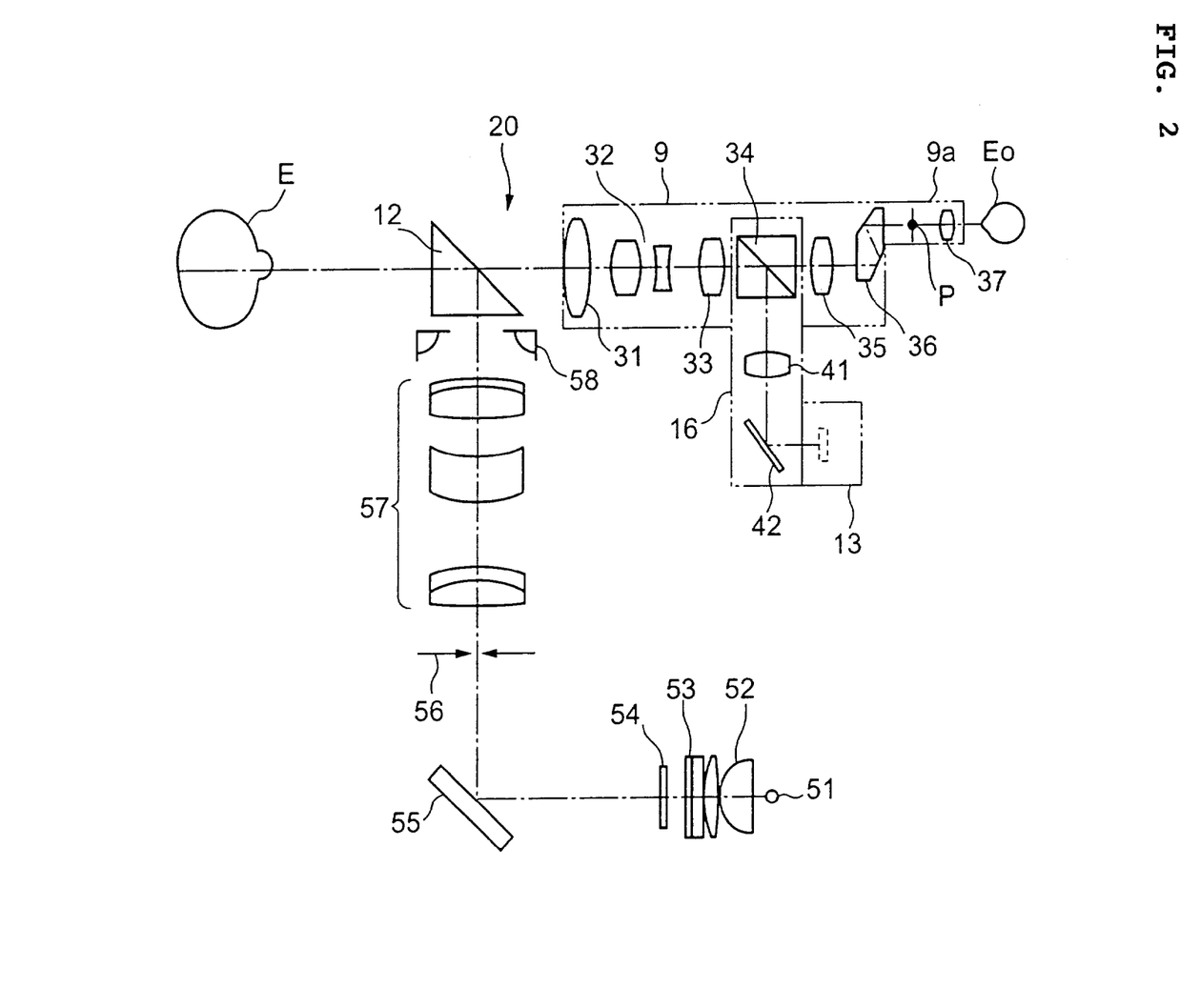
FIG. 2 is a schematic structural diagram showing an optical system and a control system in a main body according to Embodiment 1.

FIG. 2 schematically shows the optical structure of the main body 20. The main body 20 includes the illumination system 6 disposed below the prism 12 opposed to the eye to be examined E, the observation system 7 disposed orthogonal to the illumination system 6 with respect to the prism 12, the camera attachment 16, and the photographing device 13.

The illumination system 6 includes a light source 51 such as a halogen lamp, a condenser lens 52 for condensing light from the light source 51, an infrared light cutting filter 53, a color temperature converting filter 54, a mirror 55 for bending an optical path upward by 90 degrees, a slit 56 for passing only a portion of light to obtain slit light, a relay lens 57, and a light flux diaphragm portion 58 for flare cutting used in observing an eye fundus of the eye to be examined E. The prism 12 is disposed above the light flux diaphragm portion 58. Note that, although not shown in FIG. 2, the illumination system 6 further includes a background illumination section 81 for conducting background illumination in observing the eye to be examined E (see column of photographing processing mode 2 in FIG. 4).

The observation system 7 includes the prism 12, an objective lens 31, a variable optical system 32, a condenser lens 33, a relay lens 35, a prism 36 for changing an optical path to the eyepiece barrel 9a side, and an eyepiece lens 37 disposed in the eyepiece barrel 9a. Thus, the image of the eye to be examined E is imaged into an imaging point P shown in FIG. 2, so that it can be observed by an examiner's eye Eo.

Also, the camera attachment 16 includes a beam splitter 34 inserted into the optical path of the observation system 7 and a condenser lens 41 for condensing a light flux branched by the beam splitter 34 and leading it to the photographing device 13 for imaging.

FIG. 3 shows a control system of the ophthalmologic photographing apparatus 1 of Embodiment 1. The ophthalmologic photographing apparatus 1 has the control unit 40 and the image monitor 21 such as a liquid crystal display which is connected with the control unit 40 and monitors an image of the eye to be examined E. The control unit 40 includes the storage means 61 such as a ROM for storing a photographing condition related to the main body 20 and a photographing processing condition related to the photographing device 13 for each of plural kinds of photographing processing modes in photographing the eye to be examined E, the designating means 62 such as a key operating section for designating a photographing processing mode of the eye to be examined E, the control section 60 as setting means for reading out a photographing condition related to the main body 20 and a photographing processing condition related to the photographing device 13 for the corresponding photographing processing mode from the storage means 61 according to the designation by the designating means 62 and conducting the photographing condition setting to the main body 20 and the photographing processing condition setting to the photographing device 13, and the image processing means 63 for processing a photographing image.

A photographing device control cable 71 and a main body control cable 72 are used for the connection between the control unit 40 and the photographing device 13 and the connection between the control unit 40 and the main body 20, respectively, which are described above.

Next, plural kinds of photographing processing modes in photographing the eye to be examined E by the photographing device 13, a photographing condition related to the main body 20 and a photographing processing condition related to the photographing device 13 which correspond to each of the photographing processing modes, and an image of the eye to be examined which is photographed in each of the photographing processing modes will be described with reference to FIGS. 4 to 6.

With respect to the ophthalmologic photographing apparatus 1 of Embodiment 1, there are the following photographing processing modes 1 to 7.

(1) Photographing Processing Mode 1 (Diffusion Illumination Mode)

Figure 4:
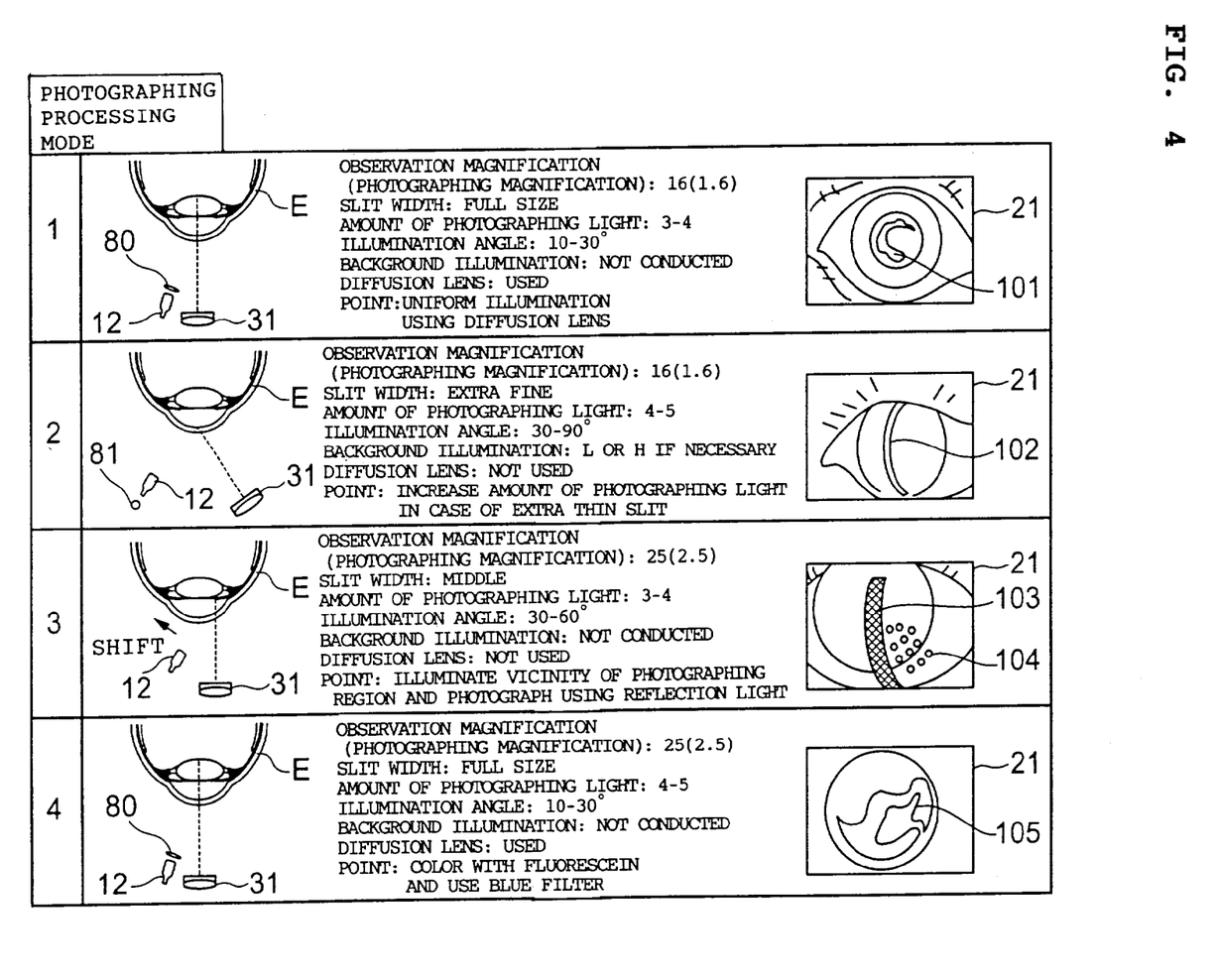
FIG. 4 is an explanatory diagram showing an arrangement between the main body and an eye to be examined, a photographing condition related to the main body, and an image of the eye to be examined which correspond to respective photographing processing modes 1 to 4 in Embodiment 1.

In the case of the photographing processing mode 1, as the photographing condition related to the main body 20 stored in the storage means 61, respective setting information (observation magnification: 16 (1.6), slit width: full size, the amount of light for photographing: 3 to 6, illumination angle: 10 degrees to 30 degrees, background illumination: not conducted, and diffusion lens 80: used) are included as shown in FIG. 4.

Also, as the photographing processing condition related to the photographing device 13, respective setting information (exposure time: Auto, Fno. (diaphragm): large, exposure correction: not conducted, sensitivity: low, gamma value: normal, photometric area: average, sharpness: normal, contrast: normal, and color: standard) are included as in the photographing processing mode 1 shown in FIG. 6.

When the respective conditions of the photographing processing mode 1 are designated by the designating means 62 and the eye to be examined E is photographed, an image of the eye to be examined which is indicated in the rightmost column of the photographing processing mode 1 shown in FIG. 4 can be photographed. Because a diffusion lens 80 is used with normal exposure, illumination light is uniformly irradiated to the entire eye to be examined, so that an image including a lesion portion 101 in the center of a screen in which a difference of image contrast is small is obtained.

(2) Photographing Processing Mode 2 (Direct Illumination Mode)

In the case of the photographing processing mode 2, as shown in FIG. 4, the background illumination section 81 is used in the illumination system 6. As the photographing condition related to the main body 20 stored in the storage means 61, respective setting information (observation magnification: 16 (1.6), slit width: extra fine, the amount of light for photographing: 4 to 5, illumination angle: 30 degrees to 90 degrees, background illumination: L (small) or H (large) if necessary, and diffusion lens: not used) are included as shown in FIG. 4.

Also, as the photographing processing condition related to the photographing device 13, respective setting information (exposure time: 1/8 seconds in maximum, Fno. (diaphragm): Auto, exposure correction: +, sensitivity: high, gamma value: normal, photometric area: high light region, sharpness: normal, contrast: normal, and color: standard) are included as in the photographing processing mode 2 shown in FIG. 6.

When the respective conditions of the photographing processing mode 2 are designated and the eye to be examined E is photographed, an image of the eye to be examined which is indicated in the rightmost column of the photographing processing mode 2 shown in FIG. 4 and in which a cornea cross sectional image 102 exists in a central region can be photographed. In the photographing processing mode 2, photographing is conducted while exposure is focused on the high light region. Thus, thin slit illumination is used and slit reflection light from the high light region is assumed as a photographing subject. However, because the amount of exposure is small, the sensitivity is increased and an exposure time is not so lengthened, thereby avoiding a blurred image. In addition, because it is preferable that the slit reflection light is bright, the exposure correction is set to "+".

(3) Photographing Processing Mode 3 (Indirect Illumination Mode)

In the case of the photographing processing mode 3, as the photographing condition related to the main body 20 stored in the storage means 61, respective setting information (observation magnification: 25 (2.5), slit width: middle, the amount of light for photographing: 3 to 4, illumination angle: 30 degrees to 60 degrees, background illumination: not conducted, and diffusion lens: not used) are included as shown in FIG. 4.

Also, as the photographing processing condition related to the photographing device 13, respective setting information (exposure time: Auto, Fno. (diaphragm): Auto, exposure correction: not conducted, sensitivity: high, gamma value: −, photometric area: spot in center, sharpness: normal, contrast: +, and color: standard) are included as in the photographing processing mode 3 shown in FIG. 6.

When the respective conditions of the photographing processing mode 3 are designated and the eye to be examined E is photographed, an image of the eye to be examined which is indicated in the rightmost column of the photographing processing mode 3 shown in FIG. 4 and in which a cornea cross sectional image 103 (indicated by a meshed area) exists like a high light in a central region can be photographed. Further, in the vicinity of the cornea cross sectional image 103, there are seen many floater images 104 (indicated with small circles) in the transparent body.

In the case of the photographing processing mode 3, illumination light is irradiated to a region different from a region for which photographing is desired, thereby illuminating the photographing region with the reflected light. The photographing region is positioned in the center of the image. Thus, spot photometry is conducted such that the exposure is not effected by the high light region and the dark region. In many cases, the photographing region is a floater in a transparent body and a low contrast, so that it is necessary to enhance a contrast.

(4) Photographing Processing Mode 4 (Fluorescence Mode)

In the case of the photographing processing mode 4, as the photographing condition related to the main body 20 stored in the storage means 61, respective setting information (observation magnification: 16 (1.6), slit width: full size, the amount of light for photographing: 4 to 5, illumination angle: 10 degrees to 30 degrees, background illumination: not conducted, and diffusion lens 80: not used) are included as shown in FIG. 4.

Also, as the photographing processing condition related to the photographing device 13, respective setting information (exposure time: Auto, Fno. (diaphragm): Auto, exposure correction: −, sensitivity: Auto, gamma value: +, photometric area: stress center and neglect high light, sharpness: +, contrast: +, and color: emphasize green) are included as in the photographing processing mode 4 shown in FIG. 6.

When the respective conditions of the photographing processing mode 4 are designated and the eye to be examined E is photographed, as indicated in the rightmost column of the photographing processing mode 4 shown in FIG. 4, a green colored region 105 which is colored with fluorescein can be photographed in an image of the eye.

In the case of the photographing processing mode 4, a contrast of the image of the eye to be examined and a green color thereof are enhanced. In addition, in order to eliminate the artificiality of the enhancement, moderate exposure is conducted.

(5) Photographing Processing Mode 5 (Crystalline Lens/Vitreous Body Mode)

Figure 5:
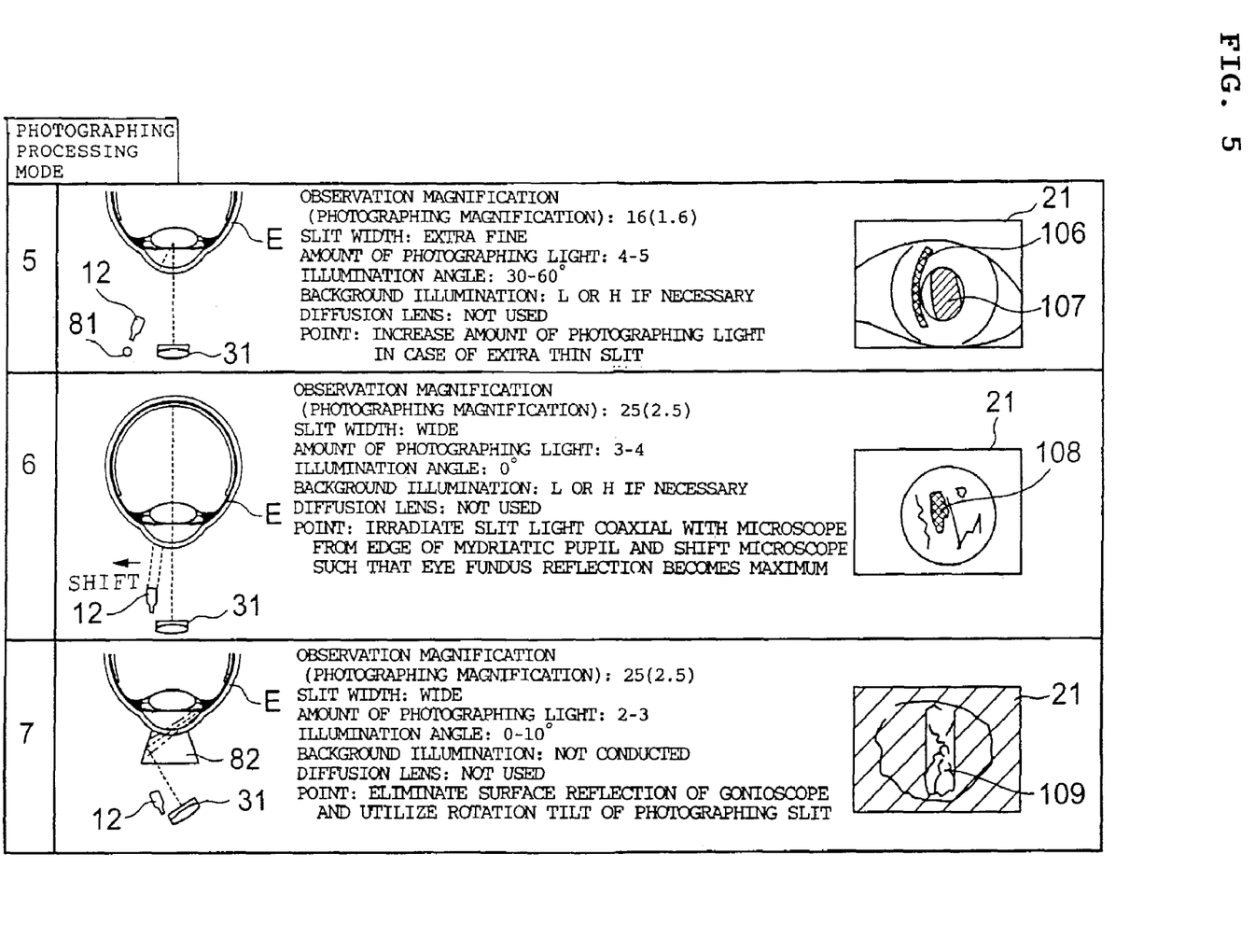
FIG. 5 is an explanatory diagram showing an arrangement between the main body and the eye to be examined, a photographing condition related to the main body, and an image of the eye to be examined which correspond to respective photographing processing modes 5 to 7 in Embodiment 1.
Figure 6:
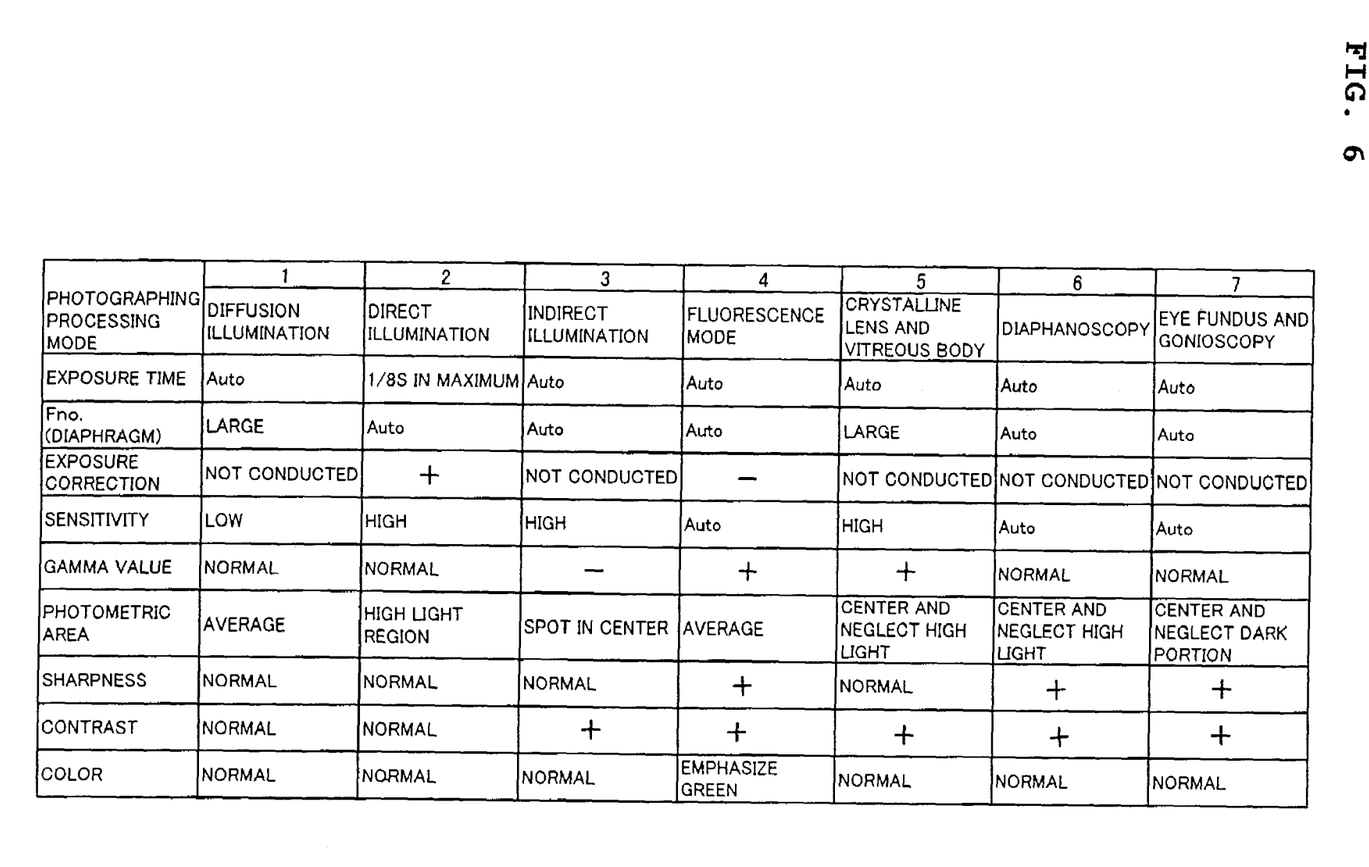
FIG. 6 is an explanatory diagram showing photographing processing conditions related to a photographing device side which correspond to the respective photographing processing modes in Embodiment 1.

In the case of the photographing processing mode 5, as shown in FIG. 5, the background illumination section 81 is used in the illumination system 6. As the photographing condition related to the main body 20 stored in the storage means 61, respective setting information (observation magnification: 16 (1.6), slit width: extra fine, the amount of light for photographing: 4 to 5, illumination angle: 30 degrees to 60 degrees, background illumination: L (small) or H (large) if necessary, and diffusion lens: not used) are included as shown in FIG. 5.

Also, as the photographing processing condition related to the photographing device 13, respective setting information (exposure time: Auto, Fno. (diaphragm): large, exposure correction: not conducted, sensitivity: high, gamma value: +, photometric area: stress center and neglect high light, sharpness: normal, contrast: +, and color: standard) are included as in the photographing processing mode 5 shown in FIG. 6.

When the respective conditions of the photographing processing mode 5 are designated and the eye to be examined E is photographed, as indicated in the rightmost column of the photographing processing mode 5 shown in FIG. 5, a cornea cross sectional image 106 (indicated by a meshed area) and a crystalline lens image 107 (indicated by a hatching area) can be photographed in an image of the eye.

In the case of the photographing processing mode 5, a depth is made deep and the gamma value is increased. In addition, thin slit light is irradiated to transparent tissues deeper than the cornea and the slit reflection light is assumed as a photographing subject. A crystalline lens and a vitreous body are thick. Thus, because a depth is made deep, a size of diaphragm is increased. Further, because intense and unnecessary reflection light exists on a cornea and a conjunctiva, it is neglected in photometry. Furthermore, the gamma value and the contrast are increased, so that a necessary region emerges.

(6) Photographing Processing Mode 6 (Diaphanoscopic Mode)

In the case of the photographing processing mode 6, as the photographing condition related to the main body 20 stored in the storage means 61, respective setting information (observation magnification: 25 (2.5), slit width: wide, the amount of light for photographing: 3 to 4, illumination angle: 0 degree, background illumination: L (small) or H (large) if necessary, and diffusion lens: not used) are included as shown in FIG. 5.

Also, as the photographing processing condition related to the photographing device 13, respective setting information (exposure time: Auto, Fno. (diaphragm): Auto, exposure correction: not conducted, sensitivity: Auto, gamma value: normal, photometric area: stress center and neglect high light, sharpness: +, contrast: +, and color: standard) are included as in the photographing processing mode 6 shown in FIG. 6.

When the respective conditions of the photographing processing mode 6 are designated and the eye to be examined E is photographed, as indicated in the rightmost column of the photographing processing mode 6 shown in FIG. 5, an eye fundus image 108 (indicated by a crossing hatching area) of the eye to be examined E is photographed like a high light.

In the case of the photographing processing mode 6, while slit light is irradiated coaxial with the optical axis of the objective lens 31 from the edge of a mydriatic pupil in the eye to be examined E, the illumination system 6 is shifted such that eye fundus reflection becomes maximum. In the photographing processing mode 6, when reflection light from a retina or the like is utilized, a subtle change and shadow on the surface of the transparent tissues can be photographed. In addition, the sharpness and the contrast are increased to enhance the subtle change. Further, because intense and unnecessary refection light exists on a cornea, it is neglected in photometry.

(7) Photographing Processing Mode 7 (Eye Fundus/Gonioscopic Mode)

In the case of the photographing processing mode 7, as the photographing condition related to the main body 20 stored in the storage means 61, respective setting information (observation magnification: 25 (2.5), slit width: wide, the amount of light for photographing: 2 to 3, illumination angle: 0 degree to 10 degrees, background illumination: not conducted, and diffusion lens: not used) are included as shown in FIG. 5. Further, an auxiliary lens (a gonioscope) 82 is used to be set in front of the eye to be examined E.

Also, as the photographing processing condition related to the photographing device 13, respective setting information (exposure time: Auto, Fno. (diaphragm): Auto, exposure correction: not conducted, sensitivity: Auto, gamma value: normal, photometric area: stress center and neglect high light, sharpness: +, contrast: +, and color: standard) are included as in the photographing processing mode 7 shown in FIG. 6.

When the respective conditions of the photographing processing mode 7 are designated and the eye to be examined E is photographed, as indicated in the rightmost column of the photographing processing mode 7 shown in FIG. 5, an eye fundus image 109 is displayed in the center of an image of the eye. A periphery of the eye fundus image 109 becomes a dark portion (indicated by a hatching area).

In the case of the photographing processing mode 7, the back of an eyeball and the edge thereof are photographed. Many dark portions exist in a region except the central region as a photographing target. Thus, the dark portions are not used for photometric computation and neglected. In addition, the sharpness and the contrast are increased to emphasize a blood vessel and the like.

(8) In addition to those, photographing processing modes corresponding to an extra fine slit image, tangential illumination, Tyndall illumination, mirror reflection, various filters, and various auxiliary lenses can be prepared.

According to the ophthalmologic photographing apparatus of Embodiment 1 as described above, the photographing condition related to the main body and the photographing processing condition related to the photographing device for each of plural kinds of photographing processing modes in photographing the eye to be examined E, which are stored in the storage means 61, are easily designated using the designating means 62 by an examiner without requiring experience. Thus, the optimum image of the eye to be examined can be simply obtained according to the designated photographing processing mode.

In other words, the examiner arbitrarily selects a desirable photographing processing mode from the group composed of the diffusion illumination mode, the direct illumination mode, the indirect illumination mode, the fluorescence mode, the crystalline lens and vitreous body mode, the diaphanoscopic mode, and the eye fundus and gonioscopic mode, which are described above, and can conduct photographing using the photographing device 13. In this case, for each of the photographing processing modes, respective setting information related to observation magnification, a slit width, the amount of photographing light, an illumination angle, a matter whether background illumination is conducted or not, and a matter whether the diffusion lens 80 is used or not are included with respect to the photographing condition related to the main body 20. In addition, with respect to the photographing processing condition related to the photographing device 13, respective setting information related to an exposure time, a size of diaphragm, a matter whether exposure correction is conducted or not, sensitivity, a gamma value, a photometric area, sharpness, a contrast, and a color are included. These information are set for the main body 20 and the photographing device 13 according to the designated photographing processing mode. Thus, the examiner can optimally photograph various images such as the lesion portion image 101 of the eye to be examined E, the cornea cross sectional images 102 and 103, the floater image 104 in the transparent body, the colored region image 105 in fluorescence photographing, the crystalline lens image, and the eye fundus image 109.

Note that the digital camera is used as the photographing device 13 in the above-mentioned Embodiment 1. A 35 mm still camera can also be used. In this case, when a photographing processing mode is set, a photographing processing condition such as film sensitivity is considered.

Note that, in addition to the above-mentioned Embodiment 1, an exposure time of the photographing device 13 can be adjusted according to the detection of the slit width. In addition, information such as a slit width of the illumination system 7, the amount of light for background illumination, an angle of the support arm 14, and a tilt angle of the observation system 6 in photographing a person to be examined can be stored so as to be useful to later photographing for the eye of the corresponding person to be examined. Further, these information can be connected with an educational-material software.

(Embodiment 2)

Next, Embodiment 2 of the present invention will be described with reference to FIGS. 7 to 10.

Figure 7:
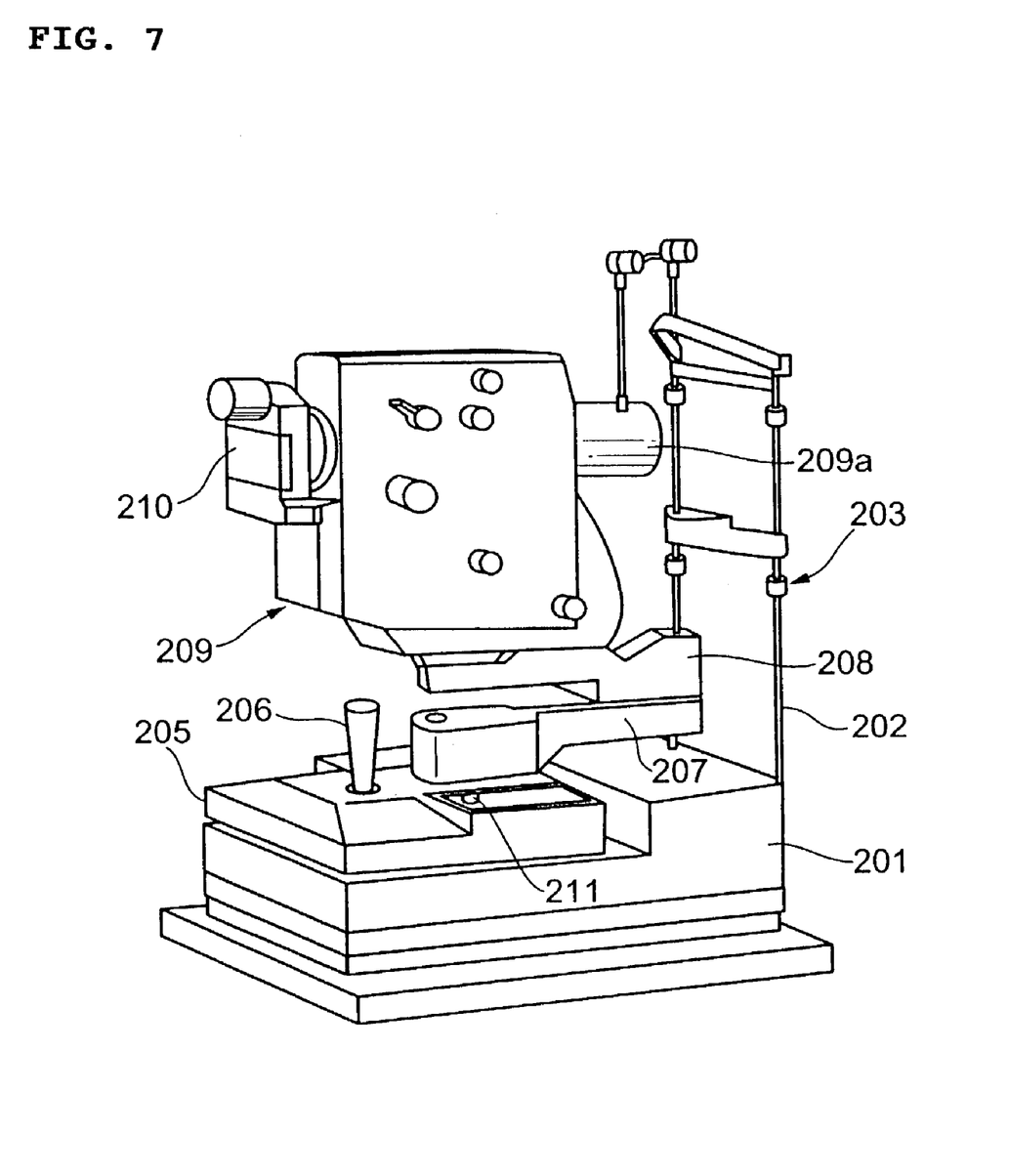
FIG. 7 is a schematic view showing the entire structure of an ophthalmologic photographing apparatus according to Embodiment 2 of the present invention.
Figure 8:
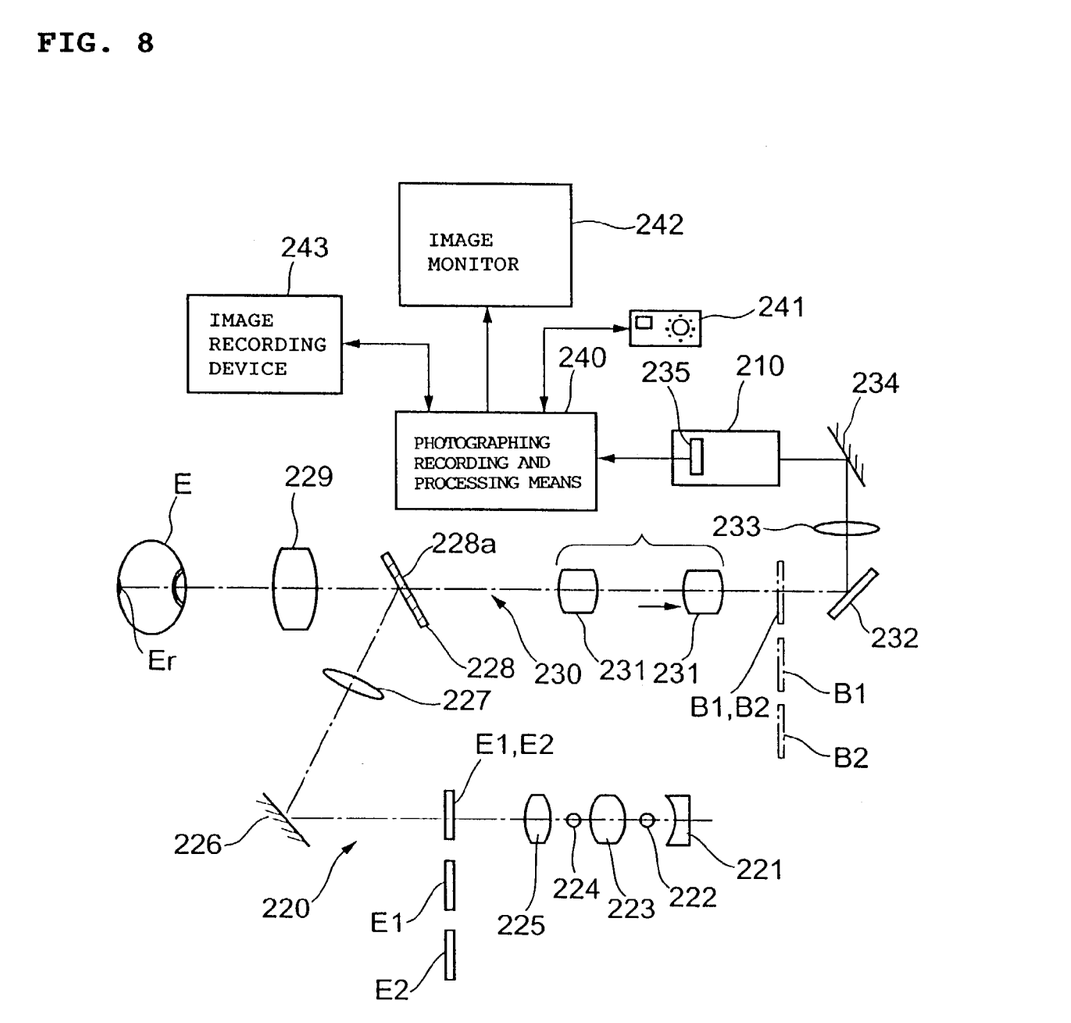
FIG. 8 is a schematic structural diagram showing an optical system and a control system in a main body according to Embodiment 2.

FIG. 7 is an outline view of an ophthalmologic photographing apparatus of Embodiment 2 and FIG. 8 is a block diagram showing an optical system and a control system in the ophthalmologic photographing apparatus of Embodiment 2.

In FIG. 7, reference numeral 201 denotes a base of the ophthalmologic photographing apparatus. A chin rest stand 203 for person to be examined, which has supporting columns 202, 202, is located on the right and left front end portions of the base 201.

A pedestal 205 is placed on the base 201. A joystick 206 is provided to the pedestal 205. The pedestal 205 can be moved right/left and forward/backward by operating the joystick 206. A main body 209 is attached to the pedestal 205 through arms 207 and 208. A barrel 209a including an objective lens of an optical system is provided protruding from the front surface of the main body 209, and a digital camera 201 as a photographing device is attached on the opposite side surface thereof. An operating switch 211 for conducting switching operation between the right eye and the left eye is attached on the pedestal 205.

Next, a structure of the optical system and that of the control system in the main body 209 will be described using FIG. 8. An illumination optical system 220 and a photographing optical system 230 are provided in the main body 209. The illumination optical system 220 is substantially composed of a concave mirror 221, a halogen lamp for illumination 222, a relay lens 223, a photographing xenon lamp 224, a condenser lens 225, a reflective mirror 226, and a relay lens 227. Illumination light is guided to an eye fundus Er of an eye to be examined E through a holed mirror 228 having a hole 228a and an objective lens 229.

The photographing optical system 230 is substantially composed of the objective lens 229, the holed mirror 228, a focal lens 231, a quick return mirror 232, a relay lens 233, a reflective mirror 234, and a color CCD 235 mounted in the digital camera 210. The focal lens 231 is adjusted by movement between a position indicated by a solid line in FIG. 8 and a position indicated by a dashed line by a drive mechanism which is not shown, thereby conducting focal operation. In FIG. 8, E1 and E2 denote an exciter filter and its dummy filter, respectively, which are insertably provided in the illumination optical system 220. In addition, B1 and B2 denote a barrier filter and its dummy filter, respectively, which are insertably provided in the photographing optical system 230.

The ophthalmologic photographing apparatus of Embodiment 2 further includes photographing recording and processing means 240, designating means 241, an image monitor 242 for displaying an image of the eye to be examined, and an image recording device 243 for recording the image information of the eye to be examined, which will be described in detail.

Figure 9:
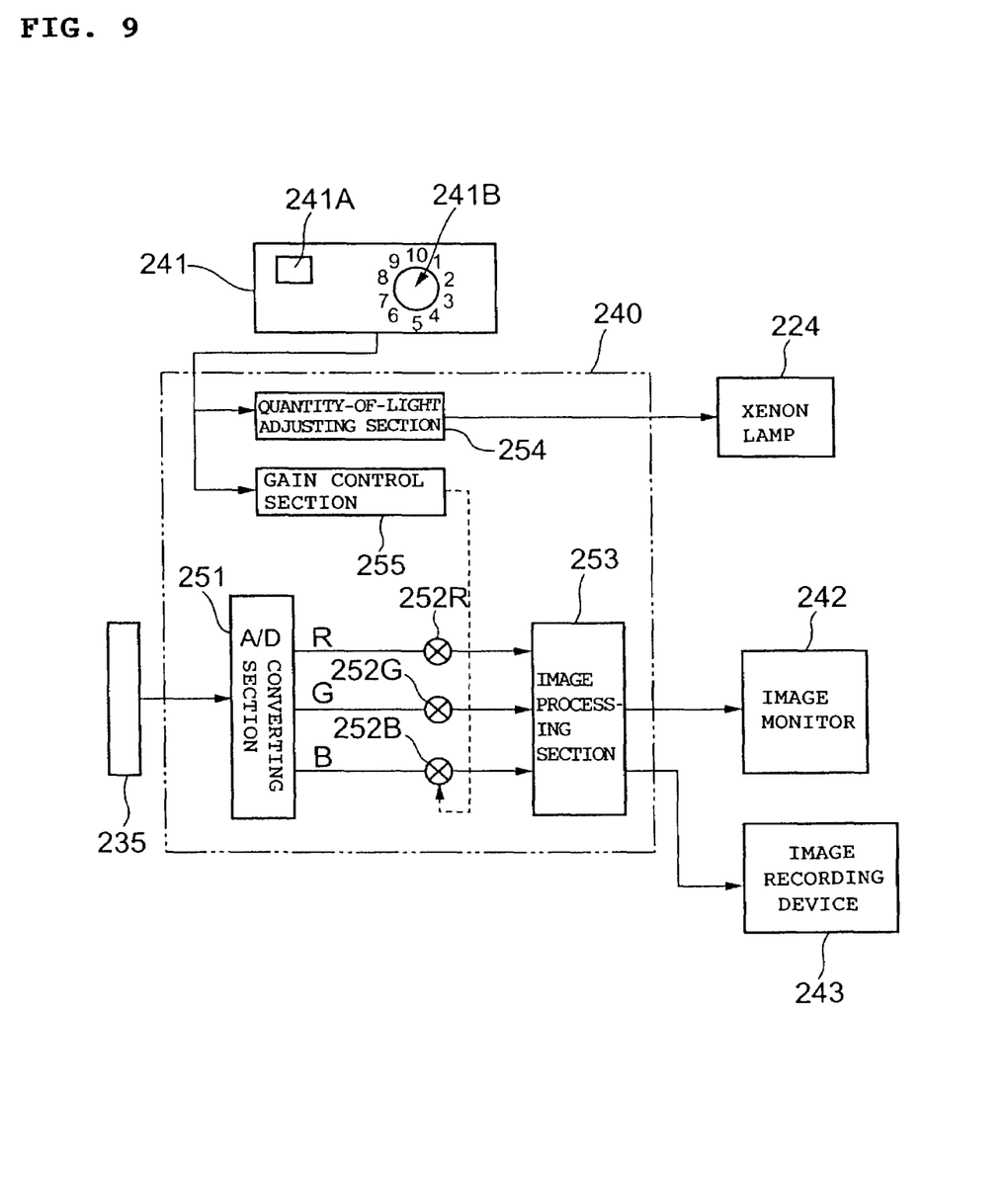
FIG. 9 is a schematic block diagram of the control system of Embodiment 2.

As shown in FIG. 9, the designating means 241 includes a mode switch 241A for designating a cataract mode to the eye to be examined E and an opacity switch 241B for designating the degree of opacity (1 to 10) by rotating operation.

The photographing recording and processing means 240 has an A/D converting section 251 for conducting A/D conversion to signal components of red (R), green (G), and blue (B) as outputs of the color image pickup device (CCD) 235 in the digital camera 210, gain controllers 252R, 252G, and 252B for conducting gain control to the A/D-converted respective signals, an image processing section 253 for conducting image processing to the respective signal components inputted from the gain controllers 252R, 252G, and 252B, a quantity-of-light adjusting section 254 for adjusting the amount of photographing light in the photographing xenon lamp 224 according to the degree of opacity designated by the opacity switch 241B, and a gain control section 255 for sending to the gain controller 252B a blue (B) gain control signal as the photographing processing condition corresponding to the degree of opacity which is related to the color image pickup device 235 in the digital camera 210 according to the degree of opacity designated by the opacity switch 241B.

Figure 10:
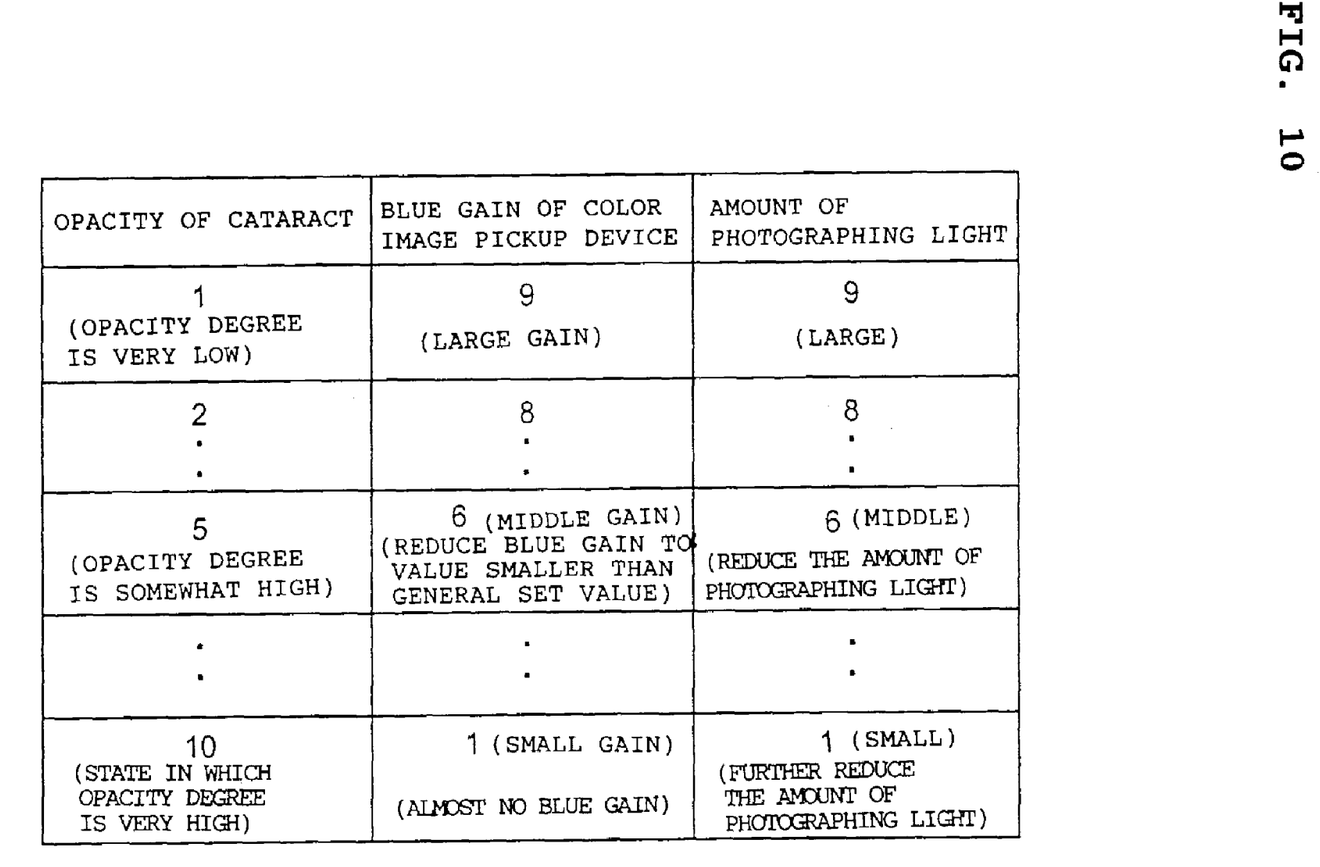
FIG. 10 is a table showing a setting example using relative numeral values for a blue gain of the color image pickup device and the amount of photographing light according to the degree of opacity of a cataract in Embodiment 2.

With respect to the degree of opacity, that is, numerals of 1 to 10, as shown in FIG. 10, numeral 1 indicates a state in which the opacity degree is very low, numeral 5 indicates a state in which the opacity degree is somewhat high, and numeral 10 indicates a state in which the opacity degree is very high. In other words, the opacity degree increases as numeral becomes larger.

With respect to the blue (B) gain control signal according to the degree of opacity, for example, as shown in FIG. 10, a blue component from the color image pickup device 235 increases as the opacity degree increases, so that blue gains of 9 (large gain), . . . , 6 (middle gain), . . . , 1 (small gain) are set as relative numeral values toward a direction in which the opacity degree increases. Thus, each suitable photographing is possible according to the degree of opacity.

With respect to the adjustment of the amount of photographing light as a photographing condition to the xenon lamp 224 by the quantity-of-light adjusting section 254 according to the degree of opacity, for example, as shown in FIG. 10, the amount of reflection light resulting from a blue component of a cataract region increases as the opacity degree increases, so that the amount of photographing light, of 9 (the amount of photographing light is substantially normal), . . . , 6 (the amount of photographing light is middle), . . . , 1 (the amount of photographing light is small) are set as relative numeral values toward a direction in which the opacity degree increases. Thus, each suitable photographing is possible without saturation according to the degree of opacity.

According to the ophthalmologic photographing apparatus of Embodiment 2, when the eye to be examined which has suffered from a cataract is photographed by the digital camera 210, the cataract mode is designated and the opacity degree is designated, so that the amount of photographing light of the xenon lamp 224 is adjusted according to the degree of opacity of the cataract to the eye to be examined E and the blue gain control to the outputs of the color image pickup device 235 is conducted according to the degree of opacity. Thus, each optimum photographing to the eye to be examined which has the cataract becomes possible according to the degree of opacity thereof.

Also, in the ophthalmologic photographing apparatus of Embodiment 2, detection means for detecting the degree of opacity of the cataract of the eye to be examined E from the amount of reflection light from the crystalline lens or the amount of transmission light passing through the crystalline lens is provided instead of using the designating means 241, and the adjustment of the amount of photographing light of the xenon lamp 224 and the blue gain control to the outputs of the color image pickup device 235 according to the degree of opacity are conducted based on a detection result of the detection means. Thus, each optimum photographing to the eye to be examined which has the cataract becomes possible according to the degree of opacity thereof.

Note that, in addition to the above-mentioned cases, an application in which information related to the degree of opacity of the cataract is sent to the image recording device 243 and a blue gain at image recording is controlled in the image recording device 243 side and an application in which a signal for changing the blue gain is send from the image recording device 243 to the gain control section 255 and the blue gain is controlled are also possible.

According to the present invention, there can be provided an ophthalmologic photographing apparatus in which a desirable photographing processing mode can be easily designated using the designating means by an examiner without requiring experience, so that the optimum images of respective regions of the eye to be examined, that is, the respective images related to the lesion portion of the eye to be examined, the cornea cross section, the floater in the transparent body, the colored region in fluorescence photographing, the crystalline lens, the eye fundus, and the like can be obtained according to the designated photographing processing mode.

Also, according to the present invention, an ophthalmologic photographing apparatus in which each photographing to the eye to be examined which has the cataract can be optimally conducted according to the degree of opacity thereof by designating the cataract mode or detecting the degree of cataract can be provided.

What is claimed is:

1. An ophthalmologic photographing apparatus comprising:
   an apparatus main body having a light source, an illumination system for irradiating an eye to be examined with illumination light and photographing light from the light source, and an observation system for observing an image of the eye to be examined which is illuminated by the illumination system;
   a photographing device having a color image pickup device, for receiving a light flux from the eye to be examined from an optical path of the observation system by the color image pickup device, photographing the image of the eye to be examined and recording the image;
   a mode switch for designating a cataract mode to the eye to be examined;
   an opacity switch for designating a degree of opacity of a cataract of the eye to be examined; and
   a gain control section for sending a blue gain control signal to a gain controller according to the degree of opacity based on a designation setting of the opacity switch.

* * * * *